United States Patent [19]

Farrell et al.

[11] Patent Number: 5,383,019
[45] Date of Patent: Jan. 17, 1995

[54] INDUCTIVELY COUPLED PLASMA SPECTROMETERS AND RADIO-FREQUENCY POWER SUPPLY THEREFOR

[75] Inventor: Regis C. Farrell, Anaheim, James J. Hornsby, Camarillo, both of Calif.

[73] Assignee: Fisons plc, Ipswich, United Kingdom

[21] Appl. No.: 49,149

[22] Filed: Apr. 19, 1993

Related U.S. Application Data

[63] Continuation-in-part of Ser. No. 497,598, Mar. 23, 1990, abandoned.

[30] Foreign Application Priority Data

Dec. 17, 1992 [GB] United Kingdom ............... 9226335

[51] Int. Cl.⁶ .................. G01J 3/30; G01N 21/73
[52] U.S. Cl. .................. 356/316; 219/121.54; 315/111.51; 250/288
[58] Field of Search ............... 356/316, 317; 315/111.21, 111.51; 219/121.54, 121.57; 250/288

[56] References Cited

U.S. PATENT DOCUMENTS

| | | | |
|---|---|---|---|
| 3,296,410 | 1/1967 | Hedger | 23/703 |
| 3,648,015 | 3/1972 | Fairbairn | 219/121 |
| 3,872,278 | 3/1975 | Boom | 219/121 P |
| 3,958,883 | 5/1976 | Turner | 315/111.51 X |
| 4,306,175 | 12/1981 | Schleicher et al. | 315/111.21 |
| 4,337,415 | 6/1982 | Dürr | 315/111.51 |
| 4,629,887 | 12/1986 | Bernier | 250/251 |
| 4,629,940 | 12/1986 | Gagne et al. | 315/111.51 |
| 4,849,675 | 7/1989 | Müller | 315/111.51 |

FOREIGN PATENT DOCUMENTS

0281157 9/1988 European Pat. Off. .

OTHER PUBLICATIONS

*ICP Information Newsletter,* vol. 2, No. 2, (Jul., 1978), pp. 51–61.

Primary Examiner—Vincent P. McGraw
Assistant Examiner—K. P. Hantis
Attorney, Agent, or Firm—Marshall, O'Toole, Gerstein, Murray & Borun

[57] ABSTRACT

The invention provides methods and apparatus for atomic emission spectroscopy and for mass spectrometry which make use of an inductively coupled radio-frequency plasma torch. A radio-frequency power supply supplies energy to a plasma induction coil via reflectometer means and a matching network. A signal indicative of reflected power generated by the reflectometer is used to set the frequency of the power supply to the resonant frequency of the matching network and plasma induction coil, thereby ensuring the maximum efficiency of power transfer irrespective of the state of the plasma. Preferably a solid state power amplifier is employed in conjunction with a lower power variable frequency oscillator. Means for ensuring proper ignition of the plasma while maintaining the frequency of the power generator within a governmentally specified frequency band are also provided.

21 Claims, 3 Drawing Sheets

INDUCTIVELY COUPLED PLASMA SPECTROMETERS AND RADIO-FREQUENCY POWER SUPPLY THEREFOR

This is a continuation-in-part of U.S. application Ser. No. 07/497,598, filed Mar. 23, 1990, now abandoned.

FIELD OF THE INVENTION

This invention relates to a method of and apparatus for atomic emission spectroscopy and mass spectrometry which make use of an inductively coupled radio-frequency (RF) plasma torch. In particular it relates to methods and apparatus for automatically maintaining optimum tuning of the torch RF power supply in response to changes in the electrical properties of the plasma, especially during its ignition.

BACKGROUND OF THE INVENTION

An inductively coupled plasma (ICP) is formed by coupling the energy from a radio-frequency (typically 2 kW at 27–50 MHz) magnetic field to free electrons in a suitable gas. The magnetic field may be produced by a two- or three-turn water-cooled coil and the electrons are accelerated around the magnetic field lines that run axially through the coil. The plasma must be struck by introducing "seed" electrons into the gas, for example by means of a spark discharge, but once these are present in sufficient quantity and have enough energy the plasma becomes self-sustaining. The power from the radio frequency field is coupled directly into the plasma which can reach 10,000° in its hottest regions. If a sample is introduced into the plasma it is atomized and may be analyzed, typically for elemental composition, by atomic emission spectroscopy or by mass spectrometry. In the former case, radiation from the plasma is spectroscopically analyzed while in the latter case ions generated in the plasma are sampled from the plasma and introduced into a mass analyzer.

In prior ICP torch power supplies the plasma induction coil is connected in a tuned circuit which is energized by an RF power generator at its resonant frequency. In this way optimum efficiency is obtained because the reflected power from the coil is minimum at the resonant frequency. However, the impedance of the coil, and hence the resonant frequency of the tuned circuit, vary with the state of the plasma. For example, there are significant changes in the resonant frequency when the plasma is ignited and when the composition of the sample and gas flows to the plasma are changed. Two solutions to this problem are known. First, a fixed-frequency RF generator may be used in conjunction with a tuned circuit and matching network comprising variable capacitors and for inductors which are motor driven in a servo-control loop arranged to maintain the resonant frequency of the coil tuned circuit at the generator frequency. Such a system is described in U.S. Pat. No. 4,629,940. Although extensively used it requires the provision of physically large and expensive variable capacitors and motors and because of the relatively slow speed at which the motors can operate, is not particularly effective at coping with sudden changes in the state of the plasma.

The second prior method, described in several variations in U.S. Pat. Nos. 3,958,883 and 4,337,415, European Patent 281157, and by H. Linn in ICP Information Newsletter 1976 vol 2 (2), employs what is known as a "free-running" oscillator in which the tuned circuit comprising the plasma induction coil is also the circuit element which determines the frequency of oscillation. Free-running oscillators automatically achieve optimum power transfer but suffer several other disadvantages in practice, for example, the major power components (e.g. thermionic tube, etc) of the RF generator must be mounted close to the plasma induction coil, resulting in a physically large torch assembly which is inconvenient in use. Free-running oscillators used for ICP torches are also more difficult to start than a fixed-frequency oscillator and are difficult to implement with solid-state electronics.

A variation of the free-running oscillator ICP torch power supply is disclosed in U.S. Pat. No. 4,629,887. In this generator, the frequency of the oscillator is determined by a parallel resonant circuit which is capacitively coupled to the plasma induction coil. The coupling capacitor and induction coil are arranged to present a substantially resistive load to the generator under normal plasma conditions. This arrangement provides improved operating stability and exhibits less frequency variation with changing plasma conditions than the conventional free-running oscillator.

It is an object of the invention to provide an ICP emission spectrometer or mass spectrometer having an improved torch RF power generator which overcomes or substantially mitigates the disadvantages of prior generators, and which can easily be implemented with solid state power devices. It is a further object to provide means by which optimum power transfer from the RF generator to the plasma is automatically maintained, irrespective of the state of the plasma.

BRIEF SUMMARY OF THE INVENTION

According to the invention there is provided an ICP Mass- or emission-spectrometer having a plasma induction coil, a radio-frequency power generator whose frequency is determined by an analogue frequency control signal and a matching network containing only fixed-value electrical components for efficiently transferring power from said generator to said plasma induction coil; said spectrometer characterized by reflectometer means disposed between said generator and said matching network for generating a signal indicative of the reflected power at the output of said generator, and frequency control loop means for generating said analogue frequency control signal in response to said signal indicative of the reflected power whereby the frequency of said RF power generator is adjusted to maintain said reflected power at a minimum.

Conveniently the RF power generator comprises a voltage-controlled oscillator (VCO) and an RF power amplifier which drives the plasma induction coil via the matching network. A reflectometer (typically a bi-directional coupler) is connected in series with the feed to the induction coil and provides a signal indicative of the reflected power at the output of the amplifier. This signal is used to automatically adjust the frequency of the RF power generator to minimize the reflected power. In this respect the power generator behaves in a similar manner as the prior "free-running" oscillators but has the advantage over the prior oscillators that the oscillator itself operates at low power and both it and the power amplifier may be located remote from the plasma induction coil. Further, the matching network does not require the variable components which are essential for the other type of prior oscillators, and because the control loop of the present invention involves no mechanical components, matching is achieved very rapidly. Another advantage of the invention over the free-running oscillators is that the power output of the oscillator may be maintained at a low level when required because unlike the prior oscillators, feedback within the oscillator itself is independent of the output power.

Preferably the power amplifier comprises solid-state amplifying devices rather than the thermionic tubes usually employed in prior generators.

In further preferred embodiments the output of the power generator is determined by an analogue power control signal and the reflectometer means may further generate a signal indicative of the forward power delivered to the matching network. Power control loop means, responsive to the signal indicative of forward power and an operator demanded power level may be provided to generate the analogue power control signal and stabilize the forward power at the operator demanded value.

Conveniently, both the frequency and power control loop means can be implemented by digital computing means, typically a microprocessor. The analogue forward and reflected power signals from the reflectometer means may be digitized and sampled at regular intervals by the computing means in which both the frequency and power control loops may be implemented in software. The computing means may generate digitized frequency and power control signals which are then converted to the corresponding analogue signals for controlling the RF power generator.

The nominal frequency of the voltage controlled oscillator and the resonant frequency of the matching network and plasma induction coil when the plasma is ignited are advantageously selected to lie in the frequency band governmentally allocated for industrial use. Limiting means may be provided for ensuring that the oscillator frequency cannot move outside this frequency band, therefore eliminating the need for heavy RF shielding of the matching network and the plasma induction coil. In order to prevent damage to the amplifier, RF generator protection means may be provided to reduce the amplifier output to a safe level when these frequency limits prevent the oscillator frequency tracking the resonant frequency of the matching network and maintaining an acceptable impedance match. This feature is especially valuable during plasma ignition because the coil impedance with an unignited plasma is typically such that the resonance of the matching network will lie outside the permitted frequency range. To facilitate ignition of the plasma, the seed electrons required may be introduced by means of plasma ignition means comprising a corona discharge from an electrode disposed in the ICP torch connected to a high-voltage oscillator which is activated by the microprocessor. To ignite the plasma, the microprocessor may start the high voltage oscillator and simultaneously switch on the power amplifier. Because the plasma is not established the oscillator frequency is likely to immediately track to the limit of its acceptable range without coinciding with the resonant frequency of the matching network and the resulting high standing wave ratio will activate the RF generator protection means. Preferably the action of the protection means will be delayed by the microprocessor for a period long enough for the plasma to become established and the oscillator to lock to the resonant frequency, but short enough to avoid damage to the amplifier before the reflected power is reduced to an acceptable level as a consequence of the oscillator locking to the resonant frequency of the matching network.

DESCRIPTION OF THE PREFERRED EMBODIMENT

Figure 1:
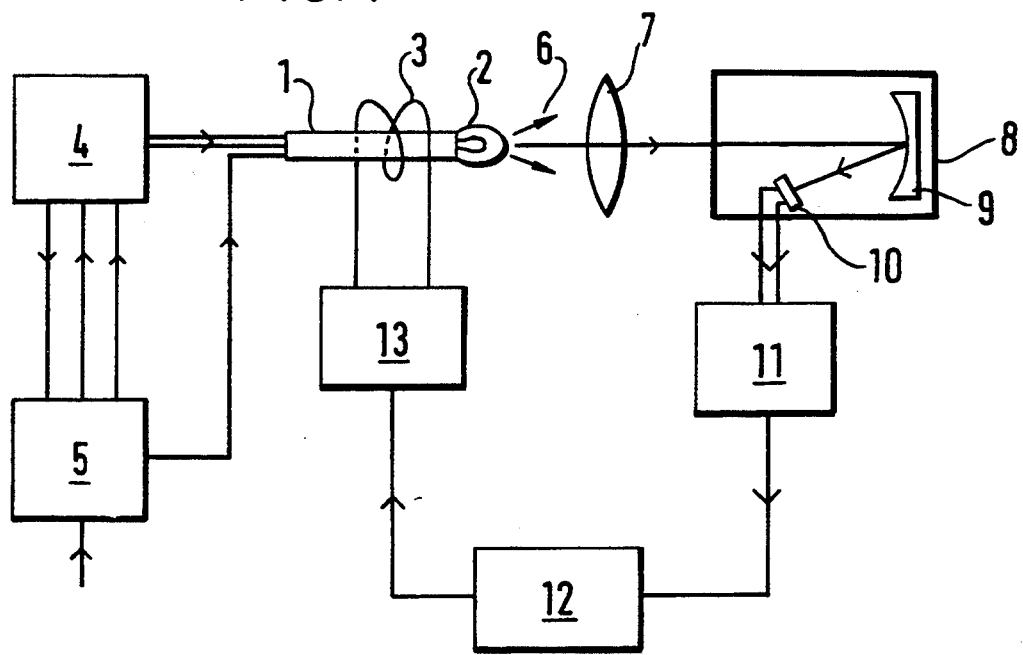
FIG. 1 is a schematic diagram of an ICP emission spectrometer according to the invention.

Referring to FIG. 1, an ICP emission spectrometer comprises an ICP torch 1 for generating a plasma 2 by means of the magnetic field generated by a plasma induction coil 3. Inert gas (usually Argon) is fed to the torch 1 by a gas supply unit 4, and a sample to be analyzed is introduced into a sample introduction device 5 which atomizes he sample by means of a nebulizer or electrothermal vaporizer and supplies it entrained in another flow of inert gas to the torch 1.

In the plasma 2, sample atoms or molecules become excited and emit spectral radiation 6 which is received by an optical transfer arrangement schematically represented by the lens 7 and transmitted to a dispersive spectrometer 8. Typically, spectrometer 8 comprises a diffraction grating 9 and a multichannel detector 10 which simultaneously records at least a portion of the spectrum produced by the grating 9. Signals from the multidetector 10 are received by a signal processor 11 which produces a spectrum of the radiation 6. A computer 12 controls the signal processor 11 and allows further processing of the spectral data.

The plasma induction coil 3 is powered by a radiofrequency power generator 13, described in detail below, which may also be controlled by the computer 12.

Figure 2:
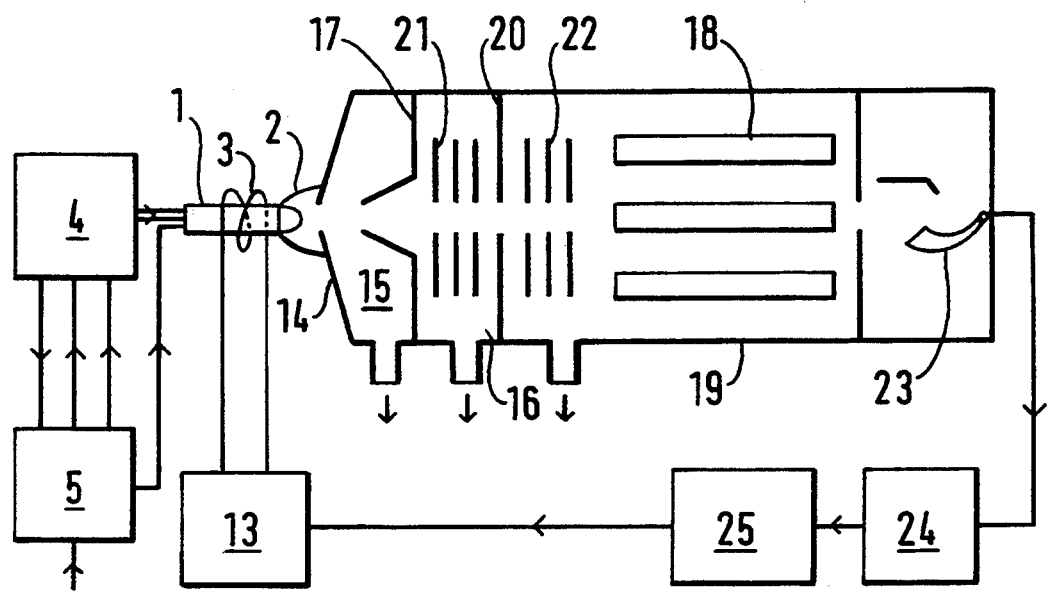
FIG. 2 is a schematic diagram of an ICP mass spectrometer according to the invention.

An ICP mass spectrometer according to the invention, shown in FIG. 2, is similar. Items 1-5 and 13 are substantially identical to the correspondingly numbered items in FIG. 2. Ions formed in the plasma 2 are sampled through a small hole in a sampling cone 14 and pass into a two-stage pressure reduction system comprising two evacuated chambers 15, 16 separated by a skimmer cone 17. A quadrupole mass filter 18, disposed in a third evacuated chamber 19, is provided to filter the ions which enter it through holes in a diaphragm 20 and the ion transfer lenses 21 and 22. An electron multiplier 23 receives the mass filtered ions from the mass analyzer 18 and an amplifier 24 and computer 25 are used to generate a mass spectrum of the ions. Computer 25 is also used to control the mass filter 18 and the plasma torch power supply 13.

Figure 3:
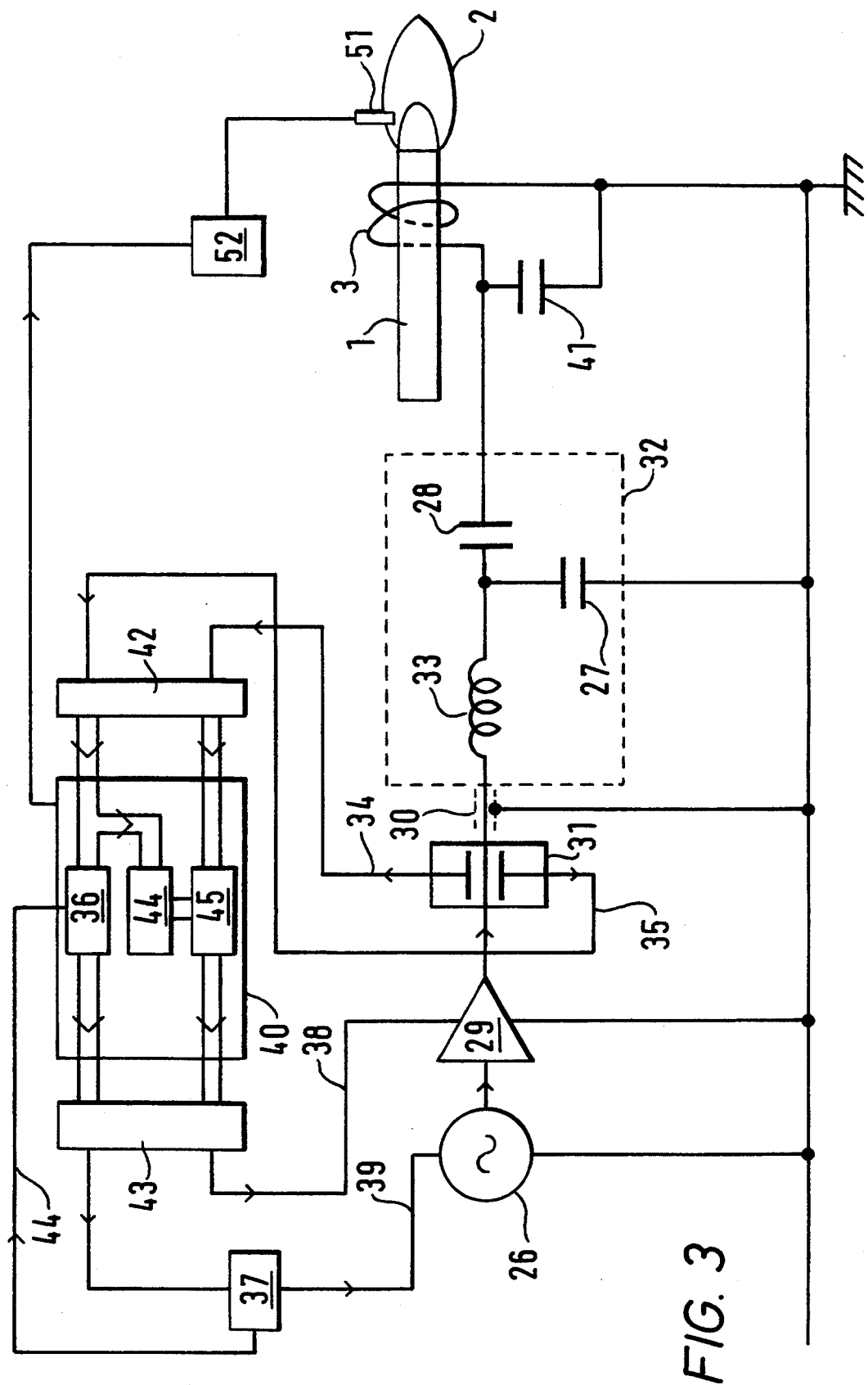
FIG. 3 is a diagram of an RF power generator suitable for use in the spectrometers of FIG. 1 and FIG. 2.

FIG. 3 shows the RF power generator 13 in greater detail. The frequency of an oscillator 26 (conveniently a voltage controlled oscillator) is determined by an analogue frequency control signal applied to its frequency control input 39. The output of the VCO 26 is coupled to the input of a solid state RF power amplifier 29 which is capable of delivering up to 2 KW of RF power into a 50 ohm load and whose output power can be set at any desired level by means of an analogue power control signal applied to its power controlling input 38.

The output of the RF power amplifier 29 is fed via reflectometer means 31 (conveniently a bi-directional coupler) and a 50 ohm impedance transmission line 30 to a matching network 32 which in turn transmits the RF power to the plasma induction coil 3. The purpose of matching network 32, which comprises fixed value capacitors 27, 28 and a fixed value inductor 33, is to efficiently transmit the power from the RF generator to the plasma. Capacitor 41 represents parallel capacitance which appears in practice across the coil 3 due to its construction. As explained, the reactance of the plasma induction coil 3 is dependent on the state of the plasma, for example whether or not it is ignited and on the nature of the sample introduced into the torch 1. The matching network 32 is located adjacent to the plasma induction coil 3.

For optimum power transfer the matching network 32 must present a 50 ohm resistive impedance to the power amplifier 29, irrespective of the reactance of the coil 3. Consequently, the matching network 32 is designed to have a resonance at the nominal frequency of the oscillator 26 when the plasma is ignited at which resonance its input impedance is arranged to be as near as possible to 50 ohm resistive. If the reactance of the plasma induction coil 3 changes due to a change in state of the plasma, the signal on the reflected power output 35 of the reflectometer 31 will increase. This signal is applied to the frequency control input 39 of the oscillator 26 via an analogue-to-digital convertor 42, a control loop means 36 (implemented in software running on a digital computer 40 provided for controlling the entire power generator) and a digital to analogue convertor 43, and causes the frequency of the oscillator 26 to be adjusted until the reflected power is minimized. In this way the frequency of the oscillator 26 is adjusted to the new resonant frequency of the matching network and optimum power transfer efficiency is maintained.

The nominal oscillator frequency under normal ignited plasma conditions is arranged to be 27.12 MHz, in the centre of frequency band governmentally specified for operation of such apparatus without extensive RF shielding. Once the plasma is ignited, the oscillator will track the resonant frequency variations which are likely to be encountered during all operations with an ignited plasma without moving outside the permitted frequency band. However, with certain torch designs the resonant frequency when the plasma is not ignited may lie outside this band. To eliminate the need for RF shielding of the induction coil 3 the control loop means 36 incorporates limiting means for preventing the VCO frequency moving outside the permitted band. These limiting means comprise a voltage comparator 37 which compares the analogue correction signal on input 39 to fixed voltage limits which correspond to the voltages which would set the VCO to the frequency limits of the permitted band. If the correction signal reaches either limit, comparator 37 generates a signal on connection 44 which prevents the control means 36 increasing the correction signal further. Consequently, the VCO frequency may not be allowed to adjust to the true resonant frequency of matching network 32 in the absence of an ignited plasma and the reflected power may rise to a high value (perhaps as high as a VSWR of 15:1).

In order to prevent damage to the amplifier 29, RF generator protection means 44 are implemented in software in digital computer 40. Protection means 44 are responsive to the magnitude of the reflected power as measured by the reflectometer 31 and operate to limit the output of amplifier 29 to a safe value (typically less than 400 W) under adverse matching conditions by means of a signal applied to a control loop means 45 (described in detail below) which controls the amplifier power output. Protection means 44 incorporates a time delay of approximately 1 second before it operates to reduce the power output of amplifier 29 to facilitate the ignition of the plasma, as discussed below.

Figure 4:
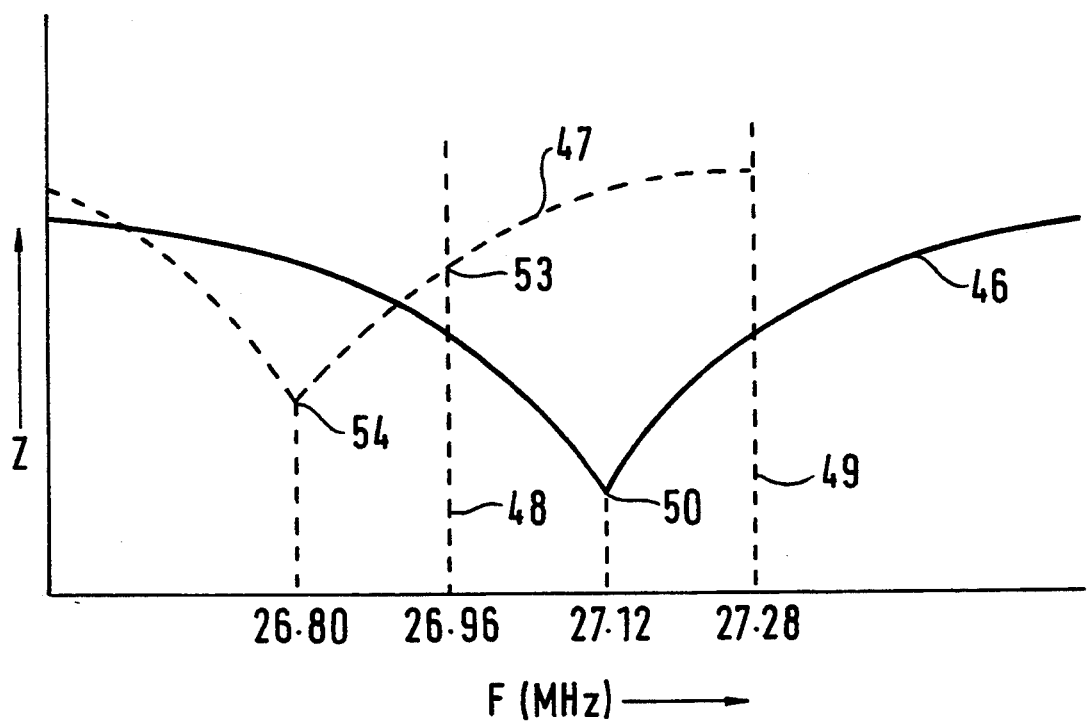
FIG. 4 is a plot of the input impedance against frequency of a matching network suitable for use in the generator of FIG. 3.

The input impedance characteristics of the matching network 32 constructed with the component values listed in Table 1 are shown in FIG. 4.

TABLE 1

| COMPONENT | VALUE |
|---|---|
| Capacitor 27 | 380 pF |
| Capacitor 28 | 112 pF |
| Inductor 33 | 126 nH |
| Plasma induction coil 3 | 393 nH |
| Stray Capacitance 41 | 5 pF |

Referring to FIG. 4, curve 46 shows the variation of the input impedance Z with frequency in the presence of an ignited plasma, and curve 47 illustrates the case in the absence of an ignited plasma. Dotted lines 48 and 49 represent the limits in which the VCO frequency is constrained to lie by the action of the voltage comparater 37 on the control loop means 36. At the point of resonance 50 on curve 46 the input impedance is substantially 50 ohm resistive so that the VSWR as monitored by reflectometer 31 is low (typically 1.05–1.20). However, FIG. 4 shows that in the absence of the ignited plasma, the resonance is less pronounced and, with the torch used in this preferred embodiment, outside the frequency range defined by limits 48, 49. Plasma ignition means comprising a discharge electrode 51 connected to a high-frequency relaxation oscillator 52 is provided to enable automatic ignition of the plasma.

The mode of operation of the system on start-up is as follows. First, the required gas flows are established in the torch 1 and the RF generator turned on. Because the plasma is not ignited, the VCO frequency will be driven to the limit 48 and the input impedance of the network 32 will be represented by the point 53 (FIG. 4). This represents a considerable mismatch so that the protection system 44 will be triggered, but this does not reduce the power output of amplifier 29 for approximately 1 second. The network is such that during this period approximately 300–400 watts of forward power is delivered to the plasma induction coil 3. Immediately the RF generator starts, computer 40 turns on the relaxation oscillator 52 which causes a discharge from the electrode 51, introducing seed electrons into the plasma and causing ionization. As a plasma begins to form, because the point 53 is within the resonant dip of curve 46, the input impedance of the matching network 32 will begin to track towards point 50 as the whole of curve 47 begins to move towards curve 46 and the input impedance falls. This favourable change in impedance is immediately translated into an increase in forward power to the coil 3 which further assists the plasma formation, moving curve 47 still closer to curve 46. As soon as the resonant point 54 in curve 47 reaches the limit 48 the VCO frequency will lock to the resonant frequency and the input impedance will tend rapidly towards a proper match, allowing the full power to be applied to the coil 3 and fully establishing the plasma. The oscillator 52 is turned off as soon as the plasma begins to form. Typically the ignition is completed before the protection system 44 causes the output power of the amplifier 29 to be reduced, but this is not essential. It is only necessary that sufficient forward power is fed to the coil 3 to maintain the movement of the curve 47 towards curve 50 until the point 54 reaches the limit 48, at which point the oscillator 26 will lock and maximum power transfer is assured. This requirement is easily met providing that point 52 lines within the resonant dip of curve 46, as indicated in FIG. 4. Matching networks to suit different types of torches, etc. may be designed according to these principles using conventional RF circuit design techniques, for example by a network analysis based on the use of a Smith chart.

Power stabilization of the RF amplifier 29 is provided by a control loop means 45, also implemented in software in computer 40, which responds to the forward power signal on output 35 of the reflectometer 31 and generates a power control signal of a power control input 38 of the amplifier 29. This loop stabilizes the power output to an operator demanded value entered into computer 40 by a keyboard or from a suitable control program. The protection means 44, after being triggered, responds after the time delay described above by overriding the demanded value and setting the output at a safe level having regard to the degree of mismatch indicated by the ratio of the reflected and forward powers measured by reflectometer 31.

The invention therefore provides an efficient method of controlling the RF generator and ensuring optimum power transfer under all conditions of the plasma. It ensures that the operating frequency always remains within the governmentally determined frequency band limits and yet provides automatic ignition of the plasma without the need for motor driven capacitors. Further, the generator can be mounted remotely from the plasma torch which greatly facilitates instrument construction.

We claim:

1. An inductively-coupled plasma mass or emission spectrometer having a plasma induction coil, a radio-frequency power generator whose frequency is determined by an analogue frequency control signal and a matching network comprising only fixed-value electrical components for efficiently transferring power from said generator to said plasma induction coil, said spectrometer characterized by reflectometer means disposed between said generator and said matching network for generating a signal indicative of the reflected power at the output of said generator and frequency control loop means for generating said control signal in response to said signal indicative of the reflected power whereby the frequency of said RF power generator is adjusted to maintain said reflected power at a minimum.

2. A spectrometer as claimed in claim 1 wherein said RF power generator comprises an oscillator whose frequency is determined by said analogue frequency control signal which drives a solid-state radio frequency amplifier, and wherein said matching network is connected to said amplifier via a transmission line.

3. A spectrometer as claimed in claim 1 wherein the output power of said RF power generator is determined by an analogue power control signal and said reflectometer means further generates a signal indicative of the forward power delivered by said generator to said matching network and wherein power control loop means, responsive to said signal indicative of the forward power and to an operator demanded power level, are provided to generate said analogue power control signal to stabilize the output of said generator to said operator demanded power level.

4. A spectrometer as claimed in claim 3 wherein said reflectometer means comprise a bi-directional coupler which generates signals indicative of both the forward and the reflected powers.

5. A spectrometer as claimed in claim 1 further comprising:
   a) analogue-to-digital conversion means for digitizing said signal indicative of reflected power,
   b) digital computing means for implementing said frequency control loop means in software, said digital computing means being responsive to said digitized signal indicative of reflected power and generating therefrom a digitized frequency control signal, and
   c) digital-to-analogue conversion means for converting said digitized frequency control signal to an analogue control signal for controlling the frequency of said power generator.

6. A spectrometer as claimed in claim 3 wherein the output power of said generator is determined by an analogue power control signal, said spectrometer further comprising:
   a) analogue-to-digital conversion means for digitizing said signal indicative of forward power;
   b) digital computing means for implementing said power control loop in software and for generating a digitized power control signal, said digital computing means being responsive to said digitized signal indicative of forward power and to said operator demanded power level; and
   c) digital-to-analogue conversion means for converting said digitized power control signal to said analogue power control signal.

7. A spectrometer as claimed in claim 1 wherein said reflectometer means generates signals indicative of both forward and reflected powers and the output of said generator is determined by an analogue power control signal, and wherein power control loop means responsive to said signal indicative of forward power and an operator demanded power level are provided to generate said analogue power control signal, said spectrometer further comprising:
   a) analogue-to-digital conversion means for digitizing both said signal indicative of forward power and said signal indicative of reverse power;
   b) digital computing means for implementing in software both said frequency control loop and said power control loop, and for generating a digitized frequency control signal in response to said digitized signal indicative of reflected power and a digitized power control signal in response to said digitized signal indicative of forward power and said operator demanded power level; and c) digital-to-analogue conversion means for respectively converting said digitized power control signal to said analogue power control signal and said digitized frequency control signal to said analogue frequency control signal.

8. A spectrometer as claimed in claim 1 wherein limiting means are provided to limit the magnitude of said analogue frequency control signal to constrain the frequency of said generator to lie within a predetermined frequency band.

9. A spectrometer as claimed in claim 1 wherein RF generator protection means responsive to said signal indicative of reflected power are provided to reduce the power output of said generator to a safe level when said reflected power exceeds a predetermined value.

10. A spectrometer as claimed in claim 9 wherein means are provided to delay the operation of said RF generator protection means for a predetermined time after said signal indicative of reflected power exceeds said predetermined value.

11. A spectrometer as claimed in claim 3 further comprising plasma ignition means operative when said generator is switched on, limiting means for limiting the magnitude of said analogue frequency control signal to constrain the frequency of said generator to lie within a predetermined frequency band, and protection means, responsive to said signal indicative of reflected power and operative a predetermined time after the reflected power exceeds a predetermined value, wherein said power control loop is also responsive to the operation of said protection means to reduce the power output of said generator to a safe level, and wherein said predetermined time is longer than the time required for the resonant frequency of said matching network to move within said predetermined frequency band during the plasma ignition process.

12. A spectrometer as claimed in claim 7 further comprising plasma ignition means operative when said generator is switched on and wherein:
   a) said digital computing means for implementing in software said frequency control loop further comprises limiting means for limiting said digitized frequency control signal to constrain the frequency of said generator to lie within a predetermined frequency band; and
   b) said digital computing means for implementing in software said power control loop means further comprises protection means responsive to said signal indicative of reflected power and operative to reduce the output power of said generator to a safe level a predetermined time after said reflected power exceeds a predetermined value; and
   c) said predetermined time is longer than the time required for the resonant frequency of said matching network to move within said predetermined frequency band during the plasma ignition process.

13. A method generating an inductively coupled plasma for use in a mass or emission spectrometer, said method comprising generating radio-frequency power at a frequency determined by an analogue frequency control signal, transmitting said power to a plasma induction coil via a matching network comprising only fixed value electrical components, generating a signal indicative of the reflected power at the input of said matching network, and generating said analogue frequency control signal in response to said signal indicative of reflected power to minimize said signal indicative of reflected power.

14. A method as claimed in claim 13 wherein said radio-frequency power is generated at a power level determined by an analogue power control signal, said method further comprising generating a signal indicative of the forward power at the input of said matching unit and generating said analogue power control signal to stabilize said signal indicative of forward power to an operator demanded level.

15. A method as claimed in claim 14 further comprising the steps of digitizing both said signals indicative of forward and reverse powers, respectively computing from said digitized signals digitized power control and digitized frequency control signals, and respectively converting said digitized power and frequency control signals to said analogue power and frequency control signals.

16. A method as claimed in claim 14 further comprising the steps of limiting said analogue frequency control signal to constrain the frequency of said generator in a predetermined frequency band, reducing after a predetermined time the output power of said generator if said signal indicative of reflected power exceeds a predetermined value.

17. A method of establishing a stable plasma in an ICP plasma emission or mass spectrometer having plasma ignition means, said method comprising the method of claim 16 and the further step of commencing to generate said RF power and simultaneously operating said plasma ignition means, and wherein said predetermined time is longer than the time required for the resonant frequency of said matching network to move within said predetermined frequency band during the plasma ignition process.

18. An inductively coupled RF plasma torch, comprising
   a) a plasma induction coil,
   b) a variable frequency RF power source,
   c) a matching network containing fixed value electrical components, and
   d) an electronic frequency control unit to minimise, in use, the RF power reflected back from the matching network to the RF power source.

19. An inductively coupled RF plasma torch according to claim 18, wherein the RF power source also has a variable output amplitude.

20. A method for tuning the plasma induction coil of an inductively coupled RF plasma torch according to claim 18, which method comprises adjusting the frequency of the variable frequency RF power source to match the resonant frequency of the coil using the electronic frequency control unit.

21. An optical emission spectrometer comprising
   a) an inductively coupled plasma torch, comprising
      i) a plasma induction coil,
      ii) a variable frequency RF power source,
      iii) a matching network containing fixed value electrical components, and
      iv) an electronic frequency control unit to minimise, in use, the RF power reflected back from the matching network to the RF power source;
   b) sample introduction means to introduce a sample to be analyzed into a plasma formed within said inductively coupled plasma torch; and
   c) detection means to measure light emitted by the sample upon atomisation in the plasma.

* * * * *